UNITED STATES PATENT

Calder, Jr.

[11] 4,224,468
[45] Sep. 23, 1980

[54] MASKING LEVEL DIFFERENCE ADAPTOR FOR AUDIOMETERS

[76] Inventor: Howard B. Calder, Jr., 2701 Hampshire Rd., Ann Arbor, Mich. 48104

[21] Appl. No.: 948,847

[22] Filed: Oct. 5, 1978

[51] Int. Cl.² ............................................. A61B 5/12
[52] U.S. Cl. .................................................. 179/1 N
[58] Field of Search ............... 128/2 Z; 179/1 N, 1 P, 179/1.5 M

[56] References Cited

U.S. PATENT DOCUMENTS

| | | | |
|---|---|---|---|
| 2,875,278 | 2/1959 | Lueders | 179/1 SW |
| 3,784,750 | 1/1974 | Stearns et al. | 179/1 N |
| 3,809,811 | 5/1974 | Delisle et al. | 179/1 N |
| 3,959,735 | 5/1976 | Grosjean | 179/1 SW |
| 4,112,377 | 9/1978 | Tanner et al. | 325/461 |

FOREIGN PATENT DOCUMENTS 1016894  10/1957  Fed. Rep. of Germany .......... 179/1 N

OTHER PUBLICATIONS

Olsen et al., "Masking Level Differences," Audiology, vol. 15, pp. 287-301, 1976.

Primary Examiner—Malcolm A. Morrison
Assistant Examiner—E. S. Kemeny
Attorney, Agent, or Firm—Reising, Ethington, Barnard, Perry & Brooks

[57] ABSTRACT

An adaptor is disclosed for use with audiometers to enable the measurement of the masking level difference (MLD) in a person's hearing capability. The adaptor comprises a signal channel and a noise (masker) channel which are connected respectively with the audiometer outputs and the earphones. Means are provided to apply the signal voltage and the noise voltage to respective mixers in the two channels and for selectively inverting the phase of the signal voltage at one of the mixers and for selectively inverting the phase of noise voltage at one of the misers. Various MLD test conditions can be established including binaural and monaural conditions and adjustable intensity at one ear.

10 Claims, 4 Drawing Figures

MASKING LEVEL DIFFERENCE ADAPTOR FOR AUDIOMETERS

TECHNICAL FIELD

This invention relates to the field of audiometry and more particularly it relates to means for measuring the masking level difference in a person's hearing capability.

BACKGROUND ART

The masking level difference (MLD) is a psychoacoustic phenomenon in which binaurally masked hearing thresholds are improved by imposing an interaural phase disparity on the signal or on the masker. The masking level difference in a given test subject is dependent upon the ability of the binaural auditory system to correlate information present in both auditory channels and, it is known that the MLD is sensitive to lesions which disrupt normal phase information. Such lesions are Meniere's disease, lesion of the VIII nerve and brainstem lesions. Abnormal MLD's in the presence of normal sensitivity has been shown to be an especially sensitive indicator of retrocochlear lesions. This is discussed by Noffsinger et al, Acta Otolaryngol (Supp) p. 303 and by Olsen et al, Audiology, Vol. 15, pp. 287–301, 1976.

A technique for measuring MLD, which has gained widespread acceptance, is described by Olsen et al, supra. In this technique, masked hearing thresholds are measured for a pure tone of 500 Hz or spondee words under one homophasic and two antiphasic conditions. These conditions are: (1) Binaural homophasic in which a signal (denoted S) is in phase with itself at the two ears of the listener (the in-phase condition denoted by capital $S_o$) and with a masker noise (denoted by N) in phase with itself at the two ears of the listener (the phase relation being denoted by $N_o$); (2) Binaural antiphasic in which the signal is 180° out of phase at the two ears of the listener (the phase relation being denoted by $S_\pi$) and the masker noise being in-phase with itself at the two ears of the listener ($N_o$); and (3) Binaural antiphasic with the signal in-phase ($S_o$) and the masker noise 180° out-of-phase ($N_\pi$) at the two ears ($S_o N_\pi$). The tone signal is obtained by a Bekesy type audiometer operating in a standard pulsed mode of stimulus presentation. The masker noise is produced by a narrow-band noise generator which produces a 600 Hz band of noise centered at 500 Hz and set to an overall level of 80 dB. The tone signal and the masker noise are supplied to a network which allows mixing of the signal and noise in a pair of earphones and allows the phase reversal of either noise or the signal in one earphone. The subjects trace their thresholds by operating the audiometer switch in the conventional manner for at least one minute under each of the above-identified test conditions. Olsen, et al, supra, also describe a technique for measuring speech MLD for spondee words using one channel of a speech audiometer for the recorded speech signal and a masker of white noise.

In the conventional clinical audiometers, typically of the Bekesy type, the test signal is supplied from a source through a variable attenuator to either side of a pair of headphones. For testing hearing threshold for pure tones, the signal source is a variable frequency audio oscillator which is set at a fixed frequency for a given test. For measuring the hearing threshold for speech, the signal source is a recorded speech signal of certain words. The audiometer is provided with a noise channel which is used to supply a selected masker or noise signal to one side of the earphones at a prescribed intensity level. The test signal is initially supplied through the attenuator at a sub-threshold level and the test subject is provided with a control switch which when actuated in one direction causes the attenuation to decrease at a given time rate of change. When the subject first hears the signal, the switch is reversed and the attenuation is progressively increased until the subject is no longer able to hear the signal and reverses the switch again. This procedure is repeated for a period of time with automatic recording of the level at which attenuation is reversed, thereby providing data for determining the subject's hearing threshold. The audiometer is required to provide a wide range of power output, on the order of 100 decibels. At the lowest level of output, the signal voltage is a small fraction of a microvolt. It is of great importance that the signal be produced at the earphones without distortion. The noise level, such as thermal noise, must be negligible compared to the lowest level of signal voltage. This type of audiometer is described in the von Bekesy U.S. Pat. No. 2,563,384.

Others have devised arrangements for supplying the audiometer signal voltage and noise voltage outputs to the earphones with selected phase inversions. A known arrangement comprises a first mixer network connected between the audiometer signal voltage output and one side of the earphones and a second mixer network connected between the noise voltage output of the audiometer and the other side of the earphones. The signal voltage is applied to the first mixer network through a phase inverting switch and a transformer and the noise voltage output is applied directly to the first mixer. Similarly, the noise voltage output is supplied through a phase reversing switch and a transformer to the second mixer and the signal voltage is supplied directly to the second mixer. One difficulty with this arrangement is that it introduces a significant amount of attenuation between the audiometer output and the earphones.

A general objective of this invention is to provide an MLD adaptor for audiometers which overcomes the disadvantages of the prior art arrangements for MLD testing. Additional objectives will be set forth below.

SUMMARY OF THE INVENTION

In accordance with this invention, an MLD adaptor is provided which can be interposed between an audiometer and a set of earphones for selectively producing MLD test conditions. This is accomplished by a single plug-in unit which includes a signal channel and a noise channel and means for mixing the signal and noise voltages and selectively inverting the phase and producing the MLD signals at the earphones with a voltage gain of unity.

Further, in accordance with the invention, an MLD adaptor is provided which is plugged in between an audiometer and a pair of earphones and which may be switched between the MLD mode and the conventional audiometer mode. This is accomplished by an arrangement in which the adaptor is completely bypassed when the MLD mode is switched off and there is no cross-talk or change in audiometer calibration.

Further, in accordance with this invention, an MLD adaptor is provided which is adaptable to any audiometer without requiring calibration or other adjustments. This is accomplished by isolation of the input of the signal channel from the input of the noise channel, preferably by utilizing a differential amplifier as a buffer at the input of the signal channel and utilizing a differential amplifier as a buffer at the input of the noise channel.

Further, in accordance with this invention, an MLD adaptor is provided for interposition between an audiometer and a pair of earphones without contributing any significant amount of thermal noise to the voltages representing the MLD conditions at the earphones. This is accomplished by providing a voltage gain amplifier at the input of each channel and a voltage attenuator at the output of each channel with the attenuation thereof being equal to the gain of the amplifier.

Further, in accordance with this invention, an MLD adaptor is provided which permits MLD testing of a subject having a hearing loss in one ear. This is accomplished by providing a variable attenuator in one of the adaptor channels, preferably in the signal channel, so that a procedure can be executed which compensates for the hearing loss.

Further, according to this invention, an MLD adaptor is provided which permits measurement of a monaural MLD. This is accomplished by an arrangement which provides a signal voltage and a noise voltage at only one earphone for establishing a reference and then providing a monaural signal voltage at one earphone and a binaural in-phase noise voltage at both earphones.

A more complete understanding of this invention may be obtained from the detailed description that follows, taken with the accompanying drawings.

BEST MODE FOR CARRYING OUT THE INVENTION

Figure 1:
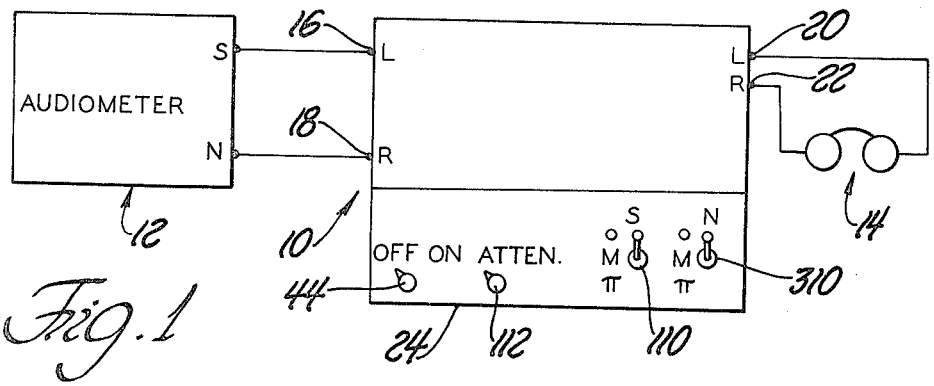
FIG. 1 is a block diagram showing the MLD adaptor of this invention in conjunction with an audiometer and a pair of earphones.

Referring now to the drawings, there is shown an illustrative embodiment of the invention in a masking level difference (MLD) adaptor 10. The adaptor 10 is interposed between a conventional audiometer 12 and a pair of earphones 14. The adaptor has a left or signal channel input 16 which is connected with the left or signal output of the audiometer. The adaptor also has a right or noise channel input 18 which is connected with the right or noise output of the audiometer 12. Most conventional audiometers provide the signal through the left output for connection with the left earphone; if an audiometer is used which presents the signal at the right output, the connections described should be reversed. The adaptor 10 is provided with a left or signal channel output 20 which is connected with the left earphone and it also has a right or noise channel output 22 which is connected with the right earphone. The adaptor 10 is provided with a control panel 24 which includes manual controls for operation of the MLD adaptor. This includes an on-off or power supply switch 44 and an attenuator 112. It also includes a selector switch 110 and a selector switch 310 for setting up the desired MLD test conditions, as will be discussed below.

Figure 2:
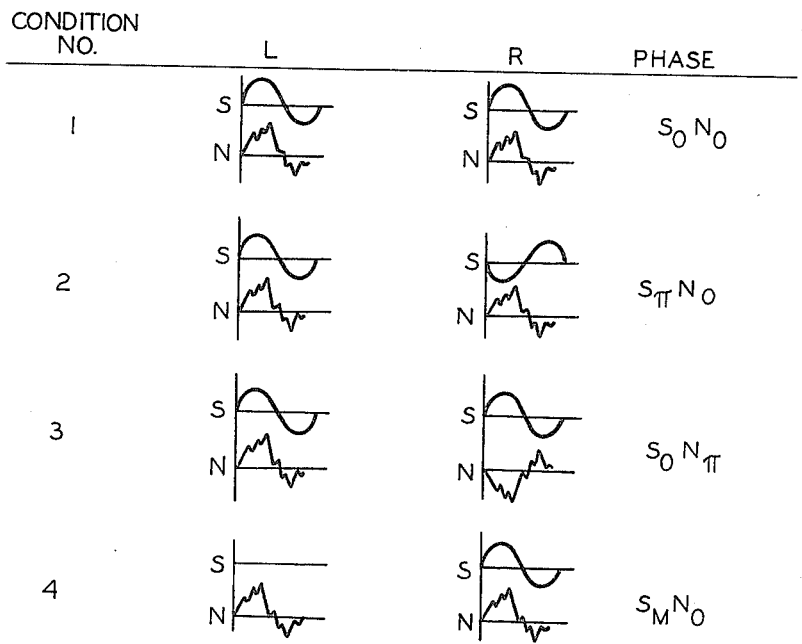
FIG. 2 is a diagrammatic representation of the MLD test conditions which can be executed with the subject invention.

The various MLD test conditions which are used in clinical audiology are represented in FIG. 2. It will be helpful to consider the various conditions prior to the description of the MLD circuitry. In the table of FIG. 2, four different test conditions are illustrated and are numbered 1 through 4 in the left-hand column labeled "Condition". In the column labeled "L" is a graphical representation of the signal voltage S and the noise voltage N applied to the left earphone of the earphones 14. Similarly, the column labeled "R" shows a graphical representation of the signal voltage S and the noise voltage N applied to the right earphone. The column labeled "Phase" denotes the phase relationship between the signal voltages at the left and right earphones respectively for each condition and the phase relationship between the noise voltages at the left and right earphones respectively for each condition. The notation is the same as that described above, namely, the subscript "o" means that the signal voltages or the noise voltages, as the case may be, are homophasically related or in-phase with each other at both earphones and the subscript "$\pi$" means that the signal voltages or noise voltages, as the case may be, are antiphasically related or out-of-phase with each other at both earphones. The subscript "M" means that the signal or noise voltage is monaural and supplied only to one earphone.

Reverting back to FIG. 1, it will be appreciated that the audiometer 12 may take a variety of forms. Modern audiometers are usually provided with a built-in signal source for providing a variable frequency pure-tone signal to the left-hand audiometer output. An external source may be connected with the left-hand output of the audiometer to provide speech or voice signals. The audiometer is provided with a built-in source of noise which is applied to the right-hand output of the audiometer. An external source of noise may be connected to the right-hand output of the audiometer. For the purpose of this description, the term audiometer is employed to mean the combination of a signal source and a noise source regardless of whether they are an integral part of the same instrument or constitute separate instruments.

Figure 4:
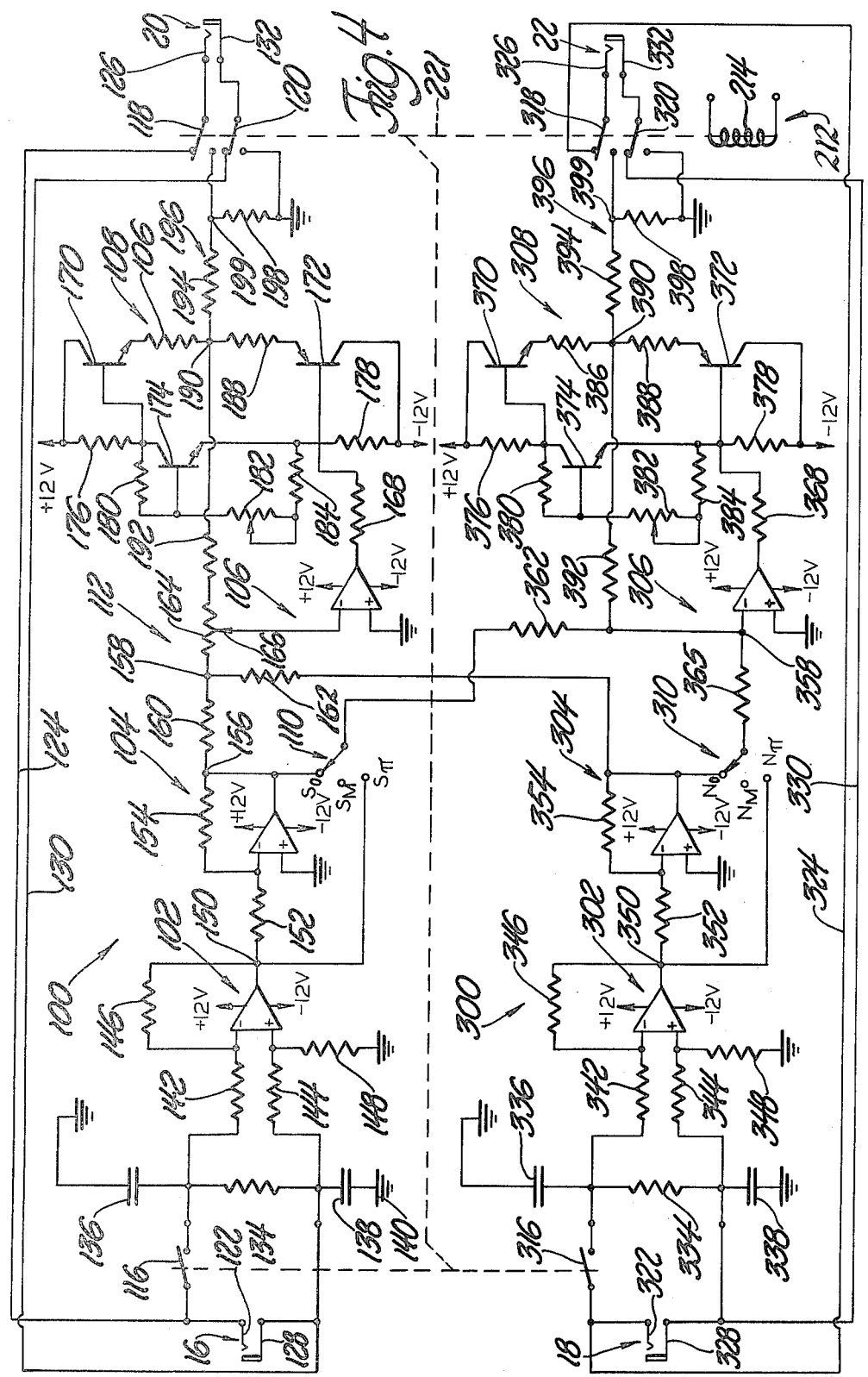
FIG. 4 is a schematic diagram of the MLD adaptor.

The masking level difference adaptor, which will be described in detail with reference to the schematic diagram of FIG. 4, is implemented by means of linear integrated circuit chips. This provides the advantages of high quality and a high degree of reliability along with compact circuitry and low power requirements.

Figure 3:
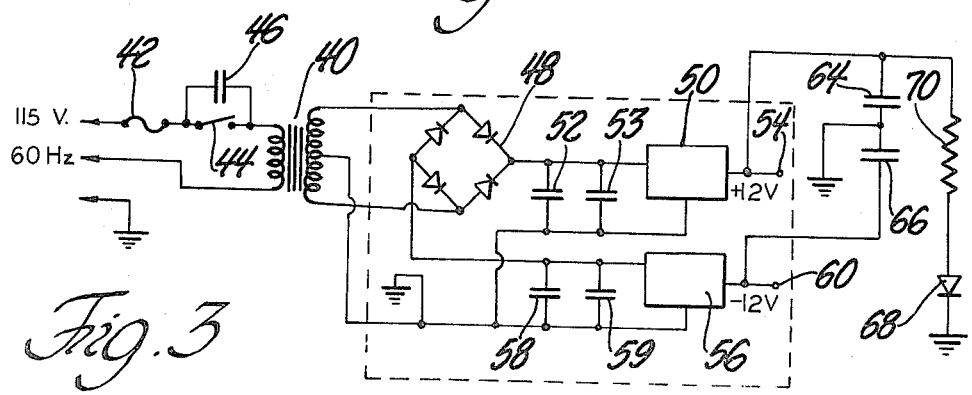
FIG. 3 is a schematic diagram of the power supply for the MLD adaptor.

The MLD adaptor is provided with a built-in power supply, as shown in FIG. 3. The power supply is of conventional design and is adapted to be energized from a standard voltage source of 115 volts AC, 60 Hz. The power supply provides a positive 12 volts DC output and a negative 12 volts DC output. The power supply comprises a power transformer 40 having a primary winding which is connected to the voltage source through a fuse 42 and a switch 44 having a switching transient bypass capacitor 46 connected thereacross. The secondary winding of the transformer is connected across a full-wave bridge rectifier 48 and the secondary winding has its center tap connected to ground. The positive output terminal of the rectifier 48 is connected to the input terminal of a voltage regulator 50. The voltage regulator 50 has a common terminal connected to ground. A filter capacitor 52 is connected across the input and a capacitor 53 is connected in parallel therewith to inhibit oscillation. A positive DC supply voltage of 12 volts is produced at the positive output terminal 54. In a similar manner, the negative terminal of the bridge rectifier 48 is connected to the input terminal of a voltage regulator 56 which has a common terminal connected to ground and a pair of capacitors 58 and 59 across the input. A negative DC supply voltage of 12 volts is produced at the output terminal 60. The voltage regulator 50 is a 3-terminal positive, fixed-voltage regulator in the form of a linear integrated circuit chip, preferably type number MCC 7812C manufactured by Motorola Semiconductor Products, Inc. The voltage regulator 56 is a 3-terminal negative, fixed-voltage regulator, Motorola type MCC 7912C. The positive supply voltage from terminal 54 and the negative supply voltage from terminal 60 is applied to the circuit of FIG. 4 at several locations as indicated symbolically by the notation "+12V" and "−12V". A capacitor 64 is connected between the supply voltage terminal 54 and ground and similarly a capacitor 66 is connected between the supply voltage terminal 60 and ground. To provide a power supply pilot light, a light emitting diode 68 is connected through a resistor 70 across the positive DC voltage at terminal 54.

The MLD adaptor circuitry will now be described with reference to FIG. 4. The adaptor comprises, in general, a signal channel 100 and a noise channel 300. The signal channel 100 is provided with the channel input 16 and the channel output 20; the noise channel 300 is provided with the channel input 18 and the channel output 22. In general, the signal channel 100 comprises a differential input amplifier 102, an inverter 104, and a mixer 106; the output of the mixer 106 is applied to a current amplifier 108 which is adapted to drive one side of the headphones 14. The noise channel 300 is similar in configuration to the signal channel and comprises an input differential amplifier 302 an inverter 304, and a mixer 306; the output of the mixer 306 is applied to a current amplifier 308 which drives the other side of the headphones 14.

In order to produce the desired test conditions at the headphones, the adaptor is provided with phase inverting means which will be described in detail below. At this point, it is noted that the phase inverting means in the signal channel 100 includes the selector switch 110 which is operative to selectively cross-couple the signal channel with the noise channel. The noise channel is provided with the selector switch 310 which is operative for intra channel coupling, whereas a fixed coupling is provided for cross-connecting the noise channel with the signal channel, as will be described below. The signal channel 100 is provided with an attenuator 112 which allows for a special test procedure, as will be described below.

The MLD adaptor is switched on or off concurrently with the switching of the power supply on or off. This is provided by a relay 212 having a coil 214 which is connected across the power supply. The relay is provided with signal channel relay contacts 116 and signal channel relay contacts 118 and 120 and it is also provided with noise channel relay contacts 316 and noise channel relay contacts 318 and 320. The aforementioned contacts are ganged as indicated by the dashed line mechanical interconnection 221. When the adaptor is turned off by opening the power supply switch 44, the relay 212 is de-energized. With the relay de-energized, the relay contacts are in the positions shown in FIG. 4. In this condition, with the adaptor turned off, the adaptor is completely bypassed and the audiometer is connected with the earphones without any affect whatsoever from the adaptor, as will be explained further below.

The signal channel input 16 and output 20 and the noise channel input 18 and output 22 take the form of conventional jacks, each having a signal contact and a common or ground contact. In the signal channel input 16, the signal contact 122 is connected to the fixed contact of relay contacts 116 and is also connected through a conductor 124 to the upper fixed contact of relay contacts 118. A signal contact 126 is connected to the fixed contact of relay contacts 118. At the signal channel input 16 the ground contact 128 is connected through a conductor 130 to the upper fixed contact of the relay contacts 120. The ground contact 132 of the signal channel output 20 is connected to the movable contact of relay contacts 120. In a similar manner, at the noise channel input 18, the signal contact 322 is connected to the movable contact of relay contacts 316 and it is also connected through a conductor 324 to the upper fixed contact of relay contacts 318. At the noise channel output 22, the signal contact 326 is connected with the movable contact of the relay contacts 318. The common or ground contact 328 of the noise channel input 18 is connected through a conductor 330 to the upper fixed contact of the relay contacts 320. The ground contact 332 of the noise channel output 22 is connected to the movable contact of the relay contacts 320. With this input-output switch arrangement for the two channels of the adaptor, the adaptor is completely bypassed when the adaptor is turned off, i.e. the power supply switch 44 is open. It is noted that the audiometer ground potential is transmitted from the ground contacts 128 and 328 of the channel inputs 16 and 18 through conductors 130 and 330, respectively, to the ground contacts 132 and 332 at the channel outputs 20 and 22. Similarly, the signal potential from the audiometer is transmitted from the signal contact 122 to the signal contact 126 on conductor 124 in the signal channel and the noise potential from the audiometer output is applied through the signal contact 322 to the signal contact 326 through the conductor 324. When the adaptor is turned on by closing the power supply switch 44, the relay 212 is energized and the relay contacts 116, 118, 120, 316, 318 and 320 are switched to the opposite position and the circuitry of the adaptor becomes operative. In this condition the bypass circuitry is disconnected.

The adaptor circuit will now be described by considering the successive stages of the signal channel 100 followed by a description of the noise channel 200. Then the interchannel selective coupling for setting up the desired test conditions will be described.

The input stage of the signal channel 100 comprises the differential input amplifier 102. The input circuit includes a load resistor 134 connected across the signal contact 122 and the ground contact 128 of the signal channel input 16. A pair of bypass capacitors 136 and 138 are connected respectively between opposite ends of the load resistor and the adaptor chassis ground 140. The input circuit additionally includes an input resistor 142 connected between the upper end of the load resistor 134 and the inverting input of the differential amplifier 102. It also includes an input resistor 144 connected between the lower end of the load resistor 134 and the noninverting input of the amplifier 102. A feedback resistor 146 is connected between the output of the amplifier 102 and the inverting input of the amplifier. A pull-up resistor 148 is connected between the noninverting input of the amplifier and ground. The differential amplifier 102 is a buffer amplifier in that it provides isolation of the input circuit from ground of the adaptor which serves to prevent cross-talk or unwanted interchannel coupling. Additionally, the amplifier 102 provides a voltage gain of a predetermined amount, which is five to one in the preferred embodiment. Attenuation in the same amount will be provided at the channel output, by means which will be described below, in order to minimize thermal noise contribution from the adaptor. The output of the differential input amplifier 102 is a phase inversion of the input signal applied to the inverting input of the amplifier. This output is derived at a node 150 and is applied to the input of the phase inverter 104.

The phase inverter 104 comprises an operational amplifier which is adapted to provide a stage gain of unity and phase inversion of the input signal. The input signal is applied from the node 150 through an input resistor 152 to the inverting input of the amplifier 104. The noninverting input of the amplifier is connected directly to ground. A feedback resistor 154 is connected between the output of the amplifier and the inverting input. The inverter develops an output signal at the node 156 which is of substantially the same voltage amplitude as the voltage at node 150 and is phase inverted with respect thereto. The output of the inverter 104 is applied to the input of the mixer 106.

The mixer 106 comprises an operational amplifier which receives an input signal on its inverting input from a summing node 158. The output of the inverter 104 at node 156 is applied to the summing node through a resistor 160. The output of the inverter 304 in the noise channel is applied through a resistor 162 to the summing node 158. The summing node 158 is connected through the attenuator 112 to the inverting input of the mixer 106. The attenuator 112 comprises a potentiometer resistor 164 and a movable contact 166. The resistor 164 exhibits a resistance value which is a logarithmic function of displacement of the movable contact. The movable contact is connected directly to the inverting input of the mixer 106. The noninverting input of the mixer 106 is connected directly to ground. The attenuator 112 provides zero attenuation when the movable contact 166 is in the extreme left-hand position and preferably provides an attenuation of 20 db when the movable contact is in the extreme right-hand position. The mixer 106 provides a voltage gain of unity and the output signal thereof is phase-inverted with respect to the input. The output signal is applied through a resistor 168 to the input of the current amplifier 108.

The current amplifier 108 is an emitter follower circuit which serves as a buffer stage to provide current amplification for driving the earphones 14. The current amplifier 108 is a push-pull complementary emitter follower and comprises an NPN transistor 170 and a PNP transistor 172. The input bias circuit for the current amplifier comprises a temperature compensated voltage source including an NPN transistor 174 having its collector connected through a bias resistor 176 to the positive DC supply voltage and having its emitter connected through a bias resistor 178 to the negative DC supply voltage. The base of the transistor 174 is connected to a voltage divider including a fixed resistor 180, a variable resistor 182 and a fixed resistor 184, the voltage divider being connected across the collector and emitter of the transistor 174. A bias voltage is applied to the base of transistor 172 from the emitter of transistor 174 and a bias voltage is applied to the base of transistor 170 from the collector of transistor 174. This bias voltage is independent of current variations but is dependent upon temperature variations so as to compensate for the temperature dependence of the amplifying transistors 170 and 172. The collector of transistor 170 is connected to the positive DC supply voltage and the emitter is connected through an emitter degeneration resistor 186 to the output node 190 of the current amplifier. Similarly, the collector of transistor 172 is connected to the negative DC supply voltage and the emitter is connected through a resistor 188 to the output node 190 of the current amplifier. A feedback path is provided from the output node 190 through a feedback resistor 192 and the attenuator resistor 164 to the inverting input of the mixer 106. The output voltage at the node 190 of the current amplifier 108 is applied to an attenuator 196.

The attenuator 196 comprises a pair of resistors 194 and 198 connected in series between the output node 190 and ground. The attenuator 196 has an output node 199 which is connected to the lower fixed contact of the relay contacts 118. The lower fixed contact of the relay contacts 120 is connected directly to ground. The attenuator 196 provides a voltage attenuation equal to the voltage gain of the preceding stages of the adaptor. As previously described, the differential input amplifier 102 provides a voltage gain of 5 and the remaining stages have a voltage gain of unity. Hence, the attenuator 196 preferably has an attenuation of 5.

The noise channel 300, with certain exceptions, is comprised of circuitry which is identical to that described above for the signal channel 100. The stages of the noise channel, namely, the differential input amplifier 302, the inverter 304, mixer 306, current amplifier 308 and attenuator 396 are the same, respectively, as the amplifier 102, inverter 104, mixer 106, current amplifier 108 and attenuator 196. In the signal channel 100, the components of the circuitry are identified by three digit reference characters having a 1 in the hundreds digit; in the noise channel 300 the same component is identified by the same reference character as in the signal channel except that there is a 3 in the hundred digit. The difference between the noise channel 300 and the signal channel 100 is as follows: (1) there is no attenuator in the noise channel which corresponds with the attenuator 112 in the signal channel, and (2) the summing node 158 at the input of the mixer 106 always receives the output of the inverter 104 and the output of the inverter 304, whereas, in the noise channel, the corresponding summing node 358 selectively receives the output of the inverter 304 or the output of the amplifier 302 and also selectively receives the output of the inverter 104 or the output of the amplifier 102. The circuitry provided for this purpose will now be described.

In order to set up the desired test conditions, phase inverting means are provided for selectively inverting the phase of the signal voltage at the mixer in one of the channels relative to the signal voltage at the mixer in the other of the channels and for selectively inverting the phase of the noise voltage at the mixer in one of the channels relative to the noise voltage at the mixer in the other of the channels. For this purpose, the selector switch 110 is provided in the signal channel and the selector switch 310 is provided in the noise channel. The selector switch 110 is a 3-position switch and is provided with a movable contact and a set of three fixed contacts $S_O$, $S_M$, and $S_\pi$. The fixed contact $S_O$ is connected directly to the output of the inverter 102 at node 156. The fixed contact $S_\pi$ is connected directly with the output of the differential input amplifier 102. The fixed contact $S_M$ is unconnected. The movable contact of the selector switch 110 is connected through a resistor 362 to the summing node 358 at the input of the mixer 306. The selector switch 310 is a 3-position switch having a movable contact and a set of three fixed contacts $N_o$, $N_M$ and $N_\pi$. The fixed contact $N_o$ is connected directly with the output of the inverter 304. The fixed contact $N_\pi$ is connected directly with the output of the differential input amplifier 302. The fixed contact $N_M$ is unconnected. The movable contact of selector switch 310 is connected through a resistor 365 to the summing node 358 at the input of the mixer 306. It is noted that in the signal channel, the input of the mixer 106 receives the output of the inverter 104 through resistor 160 and it receives the output of inverter 304 through resistor 162, this being independent of the selector switches 110 and 310. In this arrangement, selector switch 110 in the $S_o$ position applies the signal voltage to the noise channel mixer 306 in the same phase as the signal voltage applied to the mixer 106 in the signal channel. When the selector switch 110 is in the $S_\pi$ position the signal voltage applied to the mixer 306 in the noise channel is inverted with respect to the signal voltage applied to the mixer 106 in the noise channel. When the selector switch 310 is in the $N_o$ position, the noise voltage applied to the mixer 306 in the noise channel is of the same phase as the noise voltage applied to the mixer 106 in the signal channel. When the selector switch 310 is in the $N_\pi$ position, the noise voltage applied to the mixer 306 in the noise channel is opposite in phase to the noise voltage applied to the mixer 106 in the signal channel. When the selector switch 110 is in the $S_M$ position, no signal voltage is applied to the mixer 306 in the noise channel. Likewise, when the selector switch 310 is in the $N_M$ position there is no noise voltage applied to the mixer 306 in the noise channel.

A preferred embodiment of the circuit shown in FIG. 4 utilizes components of the following designation and values:

| Item | Type or Value |
| --- | --- |
| Op. Amps, all | Motorola MC 1456-CP |
| Capacitors, 136,138,336,338 | 0.001 mfd. |
| Resistors, (in ohms, ¼ watt carbon except as noted) | |
| 134, 334 | 100 (3W.) |
| *142,144,342,344 | 1K |
| *146,148,346,348 | 5K |
| *152,154,352,354 | 10K |
| *160,162 | 12.1K |
| *192 | 2.1K |
| *362,394,365 | 10K |
| 168,368 | 470 |
| 176,178,376,378 | 10K |
| 180,380 | 560 |
| 184,384 | 470 |
| 188,186,388,386 | 1 (½W) |
| 194,394 | 22 |
| 198,398 | 10 |
| Potentiometer 112 | 10K |
| Variable resistors 182,382 | 500 |
| Transistors, 170,174,370,374 | 2N6292 |
| 172,372 | 2N6107 |

*resistors are ⅛ watt, 1% metal film.

The operation of the adaptor of this invention will now be described. The adaptor 10 is connected with the audiometer 12 and the earphones 14 as described above with reference to FIG. 1. If the audiometer is to be used without the adaptor, the on-off switch knob is turned to the off position. This opens the switch 44 and the relay 212 is deenergized. With the relay deenergized, the relay contacts are in the position shown in FIG. 4. As a result, the signal channel input 16 is connected directly with the signal channel output 20 and the noise channel input 18 is connected directly with the noise channel output 22. Thus, the adaptor 10 is completely bypassed for use of the audiometer and earphones in a conventional manner. In this operating condition, the adaptor switched off, the signal channel 100 is completely isolated from the noise channel 300 and the signal paths in the respective channels are isolated from ground. Note that the ground contact 128 of signal channel input 16 and the ground contact 328 of noise channel 18 are connected by the respective plugs (not shown) from the audiometer to the audiometer ground. However, the ground contacts 128 and 328 are isolated from the chassis or ground of the adaptor by the relatively high resistors 144–148 and 344–348, respectively.

When the on-off switch knob is turned to the on position, the relay 212 is energized and the relay contacts are moved to positions opposite those shown in FIG. 4 and the adaptor 10 is operatively connected between the audiometer 12 and the earphones 14. The various test conditions, as described with reference to FIG. 2, may be selected by manipulation of the selector switch 110 and 310.

Referring now to FIG. 2, the test condition Number 1 is set up by placing the selector switch 110 in the $S_o$ position and placing the selector switch 310 in the $N_o$ position. The test conditions, Numbers 2 and 3 are established by positioning the selector switches 110 and 310 in accordance with the corresponding symbols shown in the chart of FIG. 2 under the heading "Phase". Also, a monaural test condition Number 4 may be established which provides monaural presentation of the noise to one ear. This condition is $S_M N_o$ and is established by placing selector switch 110 in the $S_M$ position and selector switch 310 in the $N_o$ position.

In addition to the test conditions illustrated in the chart of FIG. 2, the adaptor is also capable of establishing other test conditions by manipulation of the selector switches 110 and 310. A test condition $S_M N_M$, which is used for obtaining the monaurally masked threshold in conjunction with monaural MLD testing, is set up by placing the selector switches in the positions indicated by the respective subscripts. Also, a test condition $S_o N_o$ can be set up in the adaptor and may be used for obtaining the monaurally masked threshold for monaural MLD testing. Further, additional test conditions can be established by the adaptor, although they are not used routinely in clinical testing at the present time. For such additional test conditions, the selector switches 110 and 310 may be set at any desired combination of positions and each combination will provide a given test condition.

In addition to the test conditions described above, the adaptor provides for intensity adjustments to the left earphone. This is provided by the attenuator 112, as shown in FIG. 3, which is adjustable by the control knob shown in FIG. 1. Using the attenuator enables evaluation of the masking level difference for individuals having binaurally asymmetric hearing sensitivity.

Further, by reason of the use of the differential amplifiers 102 and 302 as input buffers, the adaptor is readily adaptable to any audiometer since it is not susceptible to drawing any current to ground and there is no crosstalk between channels.

Although the description of this invention has been given with reference to a particular embodiment, it is not to be construed in a limiting sense. Many variations and modifications will now occur to those skilled in the art.

What is claimed is:

1. An adaptor for audiometers to ascertain the masking level difference in a person's hearing, said audiometer having a signal voltage output and a noise voltage output, said adaptor comprising:

a signal channel having a channel input adapted to be connected with the signal voltage output of the audiometer, a signal channel mixer, and a signal channel output adapted to be connected with one earphone of a pair of earphones, a noise channel having a channel input adapted to be connected with the noise voltage output of the audiometer, a noise channel mixer and a channel output adapted to be connected with the other earphone of the pair, said channels including circuit means coupled with both of said channel inputs for applying the signal voltage and the noise voltage to the signal channel mixer and to the noise channel mixer, said circuit means including a signal channel phase inverting means for selectively inverting the phase of the signal voltage at one of said mixers relative to the signal voltage at the other of said mixers and including a noise channel phase inverting means for selectively inverting the phase of the noise voltage at one of said mixers relative to noise voltage at the other of said mixers, each of phase inverting means and each of said mixers including an amplifying device, both of said channels having a voltage gain of unity between the respective channel input and output;

wherein the signal voltages at said channel outputs are substantially equal in amplitude to the signal voltage output of the audiometer and are selectively homophasically or antiphasically related to each other and the noise voltages at said channel outputs are substantially equal in amplitude to the noise voltage output of the audiometer and are selectively homophasically or antiphasically related to each other.

2. The invention as defined in claim 1 wherein said phase inverting means comprises a signal channel phase inverter in said signal channel, a noise channel phase inverter in said noise channel, and selector switching means for applying selected ones of said signal and noise voltages to said mixers.

3. The invention as defined in claim 2 wherein said switching means includes means for selectively inverting the phase of the signal voltage at the noise channel mixer and for selectively inverting the phase of the noise voltage at the noise channel mixer.

4. The invention as defined in claim 3 wherein said switching means includes a first selector switch having a movable contact for selectively connecting the input of the signal channel inverter or the output of the signal channel inverter to the input of the noise channel mixer, and a second selector switch having a movable contact for selectively connecting the input of the noise channel inverter or the output of the noise channel inverter to the input of the noise channel mixer, said output of the noise channel inverter being connected with the input of the signal channel mixer.

5. The invention as defined in claim 4 wherein said signal channel includes a signal channel buffer amplifier coupled between signal channel input and the input of said signal channel inverter, a signal channel current amplifier connected with the output of the signal channel mixer, and a signal channel attenuator connected between the output of the signal channel current amplifier and said signal channel output, and wherein said noise channel includes a noise channel buffer amplifier coupled between the noise voltage channel input and the input of said noise voltage inverter, a noise channel current amplifier connected with the output of the noise channel mixer, and a noise channel attenuator connected between the output of the noise channel current amplifier and said noise channel output.

6. The invention as defined in claim 4 wherein said signal channel buffer amplifier has a gain equal to the attenuation of said signal channel attenuator and the remainder of said signal voltage channel has a combined gain of unity, and wherein said noise channel buffer amplifier has a gain equal to the attenuation of said noise channel attenuator and the remainder of said noise channel has a combined gain of unity, whereby the thermal noise produced by said channels is of negligible level compared to the thermal noise produced by said audiometer.

7. The invention as defined in claim 5 wherein said buffer amplifier is a differential amplifier.

8. The invention as defined in claim 2 including a power supply, a power supply switch, a relay having an energizing oil connected with the power supply and being energized by the power supply switch, said relay having contact means for connecting the signal channel input with the signal channel output and for connecting the noise channel input with the noise channel output when the power supply switch is turned off, whereby the adaptor is bypassed.

9. The invention as defined in claim 2 including a variable attenuator connected in one of said channels whereby a selectively adjustable voltage is produced at the respective channel output.

10. The invention as defined in claim 4 wherein the movable contacts of the first selector switch and the second selector switch each is selectively disconnectible from the respective inverter input or output, whereby monaural signals are presented at the earphones.

* * * * *